US005711932A

United States Patent [19]
Hirsh et al.

[11] Patent Number: 5,711,932
[45] Date of Patent: Jan. 27, 1998

[54] SCREENING PROCEDURE FOR NEUROACTIVE AGENTS

[76] Inventors: Jay Hirsh, 1905 Pheasant La., Charlottesville, Va. 22901; Chris Martin Yellman, 609 Locust Ave., Charlottesville, Va. 22902

[21] Appl. No.: 718,281

[22] Filed: Sep. 20, 1996

Related U.S. Application Data

[60] Provisional application No. 60/004,156 Sep. 22, 1995.

[51] Int. Cl.$^6$ .......................... A61K 49/00; G01N 31/00
[52] U.S. Cl. .......................... 424/9.1; 424/9.2; 435/7.2; 435/7.21
[58] Field of Search .................... 435/7.1, 7.2, 7.21; 424/9.1, 9.2

[56] References Cited

PUBLICATIONS

Zill, Journal of Neurobiolgy, 17(4):317–328; 1986.
Bicker et al, Nature, 337:33–39, 1989.
Goudey–Perriére, Comp. Biochem. Physiol., 108A(4):533–542, 1994.
Kravitz, Science, 241:1775–1781, 1988.
Tunnicliff et al, Comp. Biochem. Physiol., 29:1239–1245, 1969.
Murphy et al, The Journal of Comparative Neurology, 290:185–200, 1989.
Grossfield, New York Entomological Society, LXXXV(3):119–126, 1977.
Jurenka et al, Insect Biochem, 21(1):81–89, 1991.
Wicker et al, J. Insect Physiol., 41(1):65–70, 1995.
Truman et al, J. Exp. Biol., 61:47–55, 1974.
Vallés et al, The Journal of Comparative Neurology, 268:414–428, 1988.
Carrow et al, J. Insect Physiol., 28(5):401–404, 1982.
Hen, Comparative Molecular Neurobiology, ed. Y. Pichon., pp. 266–278, 1993.
Monastirioti et al, The Journal of Comparative Neurology, 356:275–287, 1995.
Yellman et al, Proc. Natl. Acad. Sci. 94:4131–4136, 1997.
Nijhout et al, J. Insect. Physiol., 24:293–298, 1978.
Saudou et al, The EMBO Journal, 11(1):7–17, 1992.
Burg et al, Journal of Neurobiology, 24(6):803–823, (1993).
Goudey–Perriére et al, Comp. Biochem. Physiol., 98C(2/3):407–410, 1991.

*Primary Examiner*—Marianne P. Allen
*Assistant Examiner*—Patricia A. Duffy
*Attorney, Agent, or Firm*—Sheldon H. Parker

[57] ABSTRACT

The method of testing the affect of neuroactive agents on cellular receptors is disclosed. The procedures comprise decapitating an invertebrate, in the disclosed tests a *Drosophila melanogaster* is used. A selected neuroactive agent is applied directly to the severed nerve cord of the invertebrate. The reaction of the invertebrate is observed in response to the application of the agent. The reaction of the invertebrate is an indication of the activities of the cellular receptors which react to the specific agents. The tested agents include dopamine, serotonin and octopamine and vertebrate drugs that act as D1-like receptor agonists, D1-like receptor antagonists, D2-like receptor agonists and D2-like receptor antagonist, and a vertebrate monoamine oxidase inhibitor. Other types of neuroactive agents are also used.

4 Claims, 4 Drawing Sheets

SCREENING PROCEDURE FOR NEUROACTIVE AGENTS

BACKGROUND OF THE INVENTION

1. Cross Reference to Related Application

This application is a continuation-in-part of provisional application number 60/004,156, filed Sep. 22, 1995, abandoned the disclosure of which is incorporated herein by reference, as though recited in full.

2. Field of the Invention

The invention relates the the use of decapitated invertebrates to test the reaction of specific receptors to a specific neuroactive agent through the biological reaction of the invertebrate.

3. Brief Description of the Prior Art

Many neurotransmitters and neuromodulators that have important roles in vertebrate neurophysiology are also found in the fruit fly, *Drosophila melanogaster*, and in many other simple invertebrates.

Dopamine, also known as hydroxytyramine, is a nitrogen-containing, organic compound formed during the metabolism of the amino acid tyrosine which functions as a neurotransmitter. It is well known that dopamine is an important neuromodulator in the vertebrate brain and is discussed in more detail in Dopamine receptors: Molecular biology, biochemistry and behavioral aspects, Jackson and Westlind-Danielson, *Pharmaceutical Therapy*, 64; 291–369, 1994, which is incorporated herein as though cited in full. Dopaminergic circuits are involved in many behaviors, such as the control of motor activity. Dopaminergic circuits are of great importance in that drugs of abuse, such as cocaine, affect dopamine neurotransmission. Loss of dopamine producing cells is of great clinical importance in diseases such as Parkinson's, and defective dopamine neurotransmission has been implicated in the etiology of diseases such as schizophrenia and obsessive-compulsive disorders.

Dopamine acts through a set of membrane receptors, many of which researchers have been able to clone from vertebrates. The activity of these receptors can be modulated by agonists and antagonists, but there are currently few drugs that bind with exquisite specificity for different receptor subclasses or individual receptor types. The search for new drugs with increased specificity for dopamine receptors is a major research effort in the pharmaceutical industry. Currently used screening methods include application of test drugs to cultured cells expressing the receptors, examining affects on a cAMP levels, injection the cells into rodents, and examining the rodents for behavioral changes characteristic of agonists and antagonists of various receptor subclasses. These screening methods are expensive and time consuming.

In the instant disclosure, the fruit fly is utilized as an important assay system for drugs affecting specific classes of receptors, such as dopamine, in vertebrates. Through use of decapitated flies, behavioral affects of various preparations on the nervous system can be illustrated.

SUMMARY OF THE INVENTION

The method of testing the affect of neuroactive agents on cellular receptors is disclosed. The procedure utilizes a decapitated invertebrate, in the disclosed tests a *Drosophila melanogaster* is used. A selected neuroactive agent is applied directly to the severed nerve cord of the invertebrate. The reaction of the invertebrate is observed in response to the application of the agent. The reaction of the invertebrate is an indication of the activities of the cellular receptors which react to the specific agent.

The agents used include dopamine, serotonin and octopamine and vertebrate drugs that act as D1-like receptor agonists, D1- like receptor antagonists, D2-like receptor agonists and D2-like receptor antagonist, and a vertebrate monoamine oxidase inhibitor. Other types of neuroactive agents are also used.

BRIEF DESCRIPTION OF THE DRAWINGS

The advantages of the instant disclosure will become more apparent when read with the specification and the drawings, wherein.

DETAILED DESCRIPTION OF THE INVENTION

Figure 1:
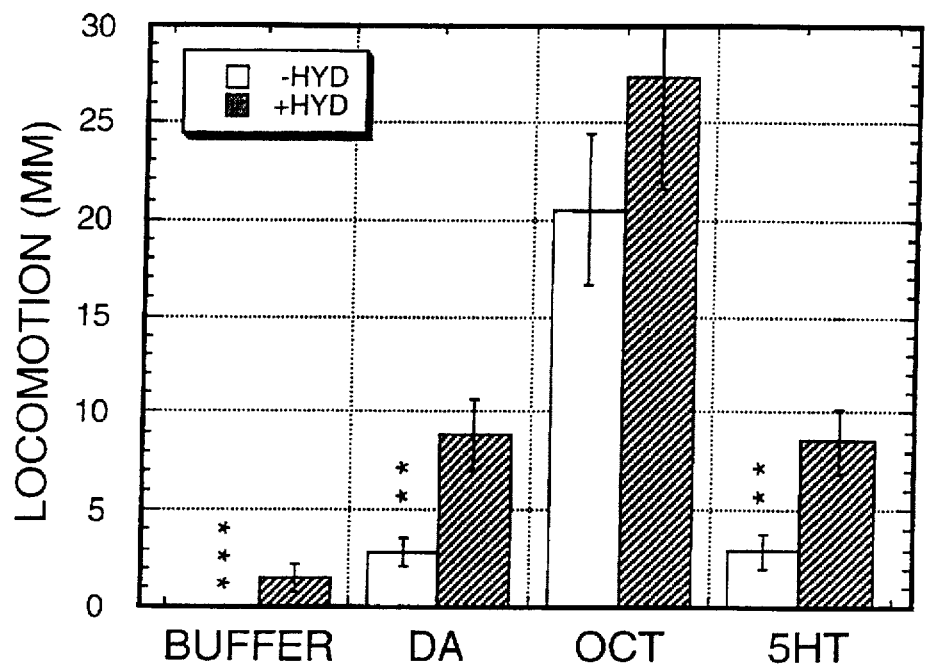
FIG. 1 is a graph illustrating the decapitated drosophila locomotion response to the amines dopamine, octopamine or serotonin alone or in conjunction with the MAO inhibitor hydrazaline.

The initial experiments set forth herein use *Drosophila melanogaster*, although this methodology can be used with many invertebrate systems. The screening protocol is rapid and inexpensive, and avoids any problems associated with the use of vertebrate animals. The disclosed system works for other neural targets as well, such as compounds interacting with receptors for serotonin and other neuroactive compounds. Alternative means of drug application, such as injection into intact animals, or application to broken body parts, cuticle or other means which will allow the agent to reach the nervous system, may also be effective. This system could further be extended by expressing vertebrate receptors in Drosophila to examine more directly interactions of drugs with these receptors.

As disclosed herein drugs known to interact with vertebrate receptors produce behavioral responses in *Drosophila melanogaster* that are similar to the responses produced when the drugs are given to vertebrates. These responses, unlike vertebrates, do not require the head or brain of the fly as they are mediated through neurons in the nerve cord. This allows the agent to be applied to the test subjects in a method which allows for direct easy application to the target neural tissue with an immediate response. Decapitated insect bodies have been used in the prior art to demonstrate that the remaining nervous system is sufficient for simple forms of learning and that it can still respond to stimulation of bristles. Therefore, if a bristle is stimulated, the body will respond by moving a leg to the site of stimulation in an attempt to groom the stimulated bristle.

In the disclosed invention, however, the decapitated flies are used as test vehicles to determine the reaction of specific neuroactive agents on the nervous system. In this way, pharmaceuticals can be tested to determine their affect on identified receptors without the controversial involvement of vertebrate animals. Although any invertebrate capable of behavioral activity after decapitation can be use, Drosophila provide current advantages. The Drosophila have a more defined genetic background than other invertebrates. Further Drosophila allow for the integration and expression of genes from other animals. For these, and other reasons, the Drosophila are used extensively in laboratories.

A number of additional agents affecting amine and related pathways in vertebrates have been tested that show striking behavioral responses in decapitated Drosophila. Cocaine and methamphetamine are two highly addictive drugs of abuse in humans that affect synaptic re-uptake of dopamine and/or serotonin. In mice, the response to cocaine is abolished when the presynaptic dopamine transporter is eliminated genetically, showing the dopamine and not serotonin is the crucial target. When cocaine is added to the nerve cord of decapitated flies, it leads to an initial response of extreme uncoordinated hyperactivity, with the flies often jumping out of the field of view. This hyperactivity persists for only a few minutes, at which time the behaviors gradually become more coordinated and transition into a response of grooming and locomotion similar to the response to the D2-like agonist quinpirole. This change in behaviors with time is due to rapid inactivation of the drug, similar to the situation in vertebrates, since applying a second dose of cocaine stimulates the same behavioral responses as the initial dose.

Methamphetamine leads to a rigid akinesic state from which the flies do not quickly recover. In vertebrates, methamphetamine blocks synaptic re-uptake of both serotonin and dopamine, which may explain the difference in response vs. the response to cocaine.

Yohimbine is an antagonist of vertebrate alpha2-adrenergic receptors. In Drosophila, a tyramine/octopamine receptor is the closest homolog to the adrenergic receptor family of genes. Yohimbine leads to an akinesic state, and is a more effective antagonist for octopamine stimulated responses than for behavioral responses to dopamine or to the D2-like agonist quinpirole. These results indicate that yohimbine and octopamine are likely acting on receptors distinct from those stimulated by the dopaminergic drugs.

In vertebrates, the cholinergic system appears to act in opposition to the dopamine system, and early therapeutics for Parkinson's disease were cholinergic antagonists. Our evidence indicates that the same relationship may hold in flies. In decapitated flies, a cholinergic antagonist, trihexylphenidyl, stimulates both locomotion and grooming, in a manner similar to the action of the D2-like agonist quinpirole.

In both vertebrates and invertebrates, the basic neural oscillators controlling reflex behaviors and locomotion are contained within the spinal cord, or the nerve cord in the case of invertebrates. Several non-human vertebrates show both locomotion and reflex scratching behaviors in response to irritants even after the spinal cord is cut. Similarly, decapitated insects show a basal level of spontaneous grooming as well as a normal grooming response when a sensory bristle is stimulated by gentle mechanical contact.

Many of these behaviors can be stimulated by application of biogenic amines. Injection of L-DOPA and 5-HTP, the precursors for dopamine/noradrenaline and serotonin, respectively, can initiate walking motor patterns in spinal cats and rabbits, although a more recent study shows that adrenergic agents are most the effective. Similarly, in partly dissected preparations of moth and locust, addition of dopamine or octopamine to the thoracic ganglia leads to stimulation of flight motor and stepping oscillators, and in cockroaches, dopamine can stimulate an escape response.

These applications of exogenous biogenic amines likely mimic the roles of amines and/or noradrenaline provided to the nerve or spinal cord from the brain by descending projections which are found in both vertebrates and in insects. The invertebrate nerve cord differs from the higher vertebrate spinal cord in that the nerve cord contains aminergic cells bodies. Presumably these cell bodies provide localized sources of amines to regions of the nerve cord neuropil that are not accessed by the descending aminergic projections.

In vertebrates and invertebrates, dopamine and other amines act through families of G protein linked seven transmembrane receptors. Stimulation or inhibition of vertebrate dopamine receptors in the brain by class-specific agonists can either stimulate or repress locomotion and stereotyped behaviors, such as grooming, sniffing, rearing and chewing behaviors. The dopamine receptors can be classified into two general classes of receptors, the D1-like and D2-like receptors, which differ in structure, in how they are linked to adenyl cyclase, and in the physiological responses that they mediate.

A severe problem limiting behavioral studies of drugs affecting amine function in insects is that the insect CNS is covered by a neuroepithelium, such that injection of drugs is often ineffective. Decapitation of the Drosophila allows direct addition of drugs to the nerve cord, and assessment of effects on grooming and locomotor behaviors. The decapitated flies maintain a normal standing posture, and show a low level of spontaneous grooming as well as a provoked grooming response, and a vigorous righting response. Flies prepared in this method are used to study the behavioral pharmacology of these responses.

The following testing has determined that dopamine, octopamine and serotonin stimulate locomotion and grooming, and that drugs specific for vertebrate dopamine receptors can modulate these behaviors. Additionally, many of these agents show sexual dimorphisms in their responses. This testing procedure opens a new preparation for functional studies of amine receptors in a genetically tractable model system.

MATERIALS AND METHODS

Decapitated flies of $w^{1118}$ *Drosophila melanogaster* were prepared by cutting heads from $CO_2$ anesthetized flies with a Dewecker Iris scissors (E. F. Fullam, Inc). Flies used for decapitation were maintained on a 12 hour light; 12 hour dark cycle, and studies were performed near the middle of their subjective day. Flies younger than 8 hr. post eclosion were not used to allow for maturation. Exposure to $CO_2$ during decapitation was minimized and limited to 5 min. since longer exposure to $CO_2$ severely limits behavioral responses. The decapitated flies were allowed to recover for 0.5 to 2 hr. in a humidified container. Only those decapitated flies that showed an upright posture and an evoked grooming response following stimulation of a thoracic bristle with a single hair of a fine paintbrush were used in further studies.

Drugs were made up in water, either as recommended by the manufacturer, or at 10 mM NaPi, pH 6. Drugs were applied to the exposed nerve cord at the anterior notum as a droplet with a micropipettor, maintaining contact with the nerve cord for 4–5 secs. Room temperature was maintained at 22–24 C., and illumination was through a fiber optic illuminator equipped with a heat filter.

Hindleg and foreleg grooming were monitored separately, as well as locomotion, responsiveness and hyperactivity. These were assayed over a 2 min observation interval, as determined by monitoring videotapes of the treated flies on a grid of 1 mm graph paper.

The technician quantitating the behaviors was ignorant of the drugs given. Grooming was counted only when the given legs were moving and in contact with either the legs or the body. Hyperactive behavior was counted as the time the animals lacked motor control, evidenced by high levels of leg activity and/or wing buzzing causing them to fall over or flip upside down. For all drugs used in this study, lower concentrations of drugs produced the same behaviors but with lessened frequency and/or with an increased delay of onset.

Biogenic amines were used at 10 mM unless otherwise noted. All receptor agonists and antagonists used in the tests were from RBI, Inc, and amines were from Sigma, although other manufactures can be used. Activities of the drugs used in this study are summarized in the following table.

TABLE 1

| DRUG | ACTIVITY |
| --- | --- |
| SCH 23390, SKF 85366 | D-1 like antagonist |
| SKF 82958, SKF 81297 | D-1 like agonist |
| eticlopride, raclopride | D-2 like antagonist |
| quipirole | D2-like agonist |
| hydrazaline | Monoamine oxidase inhibitor |

For statistical analyses one, two or three way type I sums of squares ANOVA analyses were performed using the General Table Linear Models procedure of as set forth in SAS/STAT User's Guide, Cary, N.C. SAS Institute, the contents of which are incorporated herein as though recited in full. The datasets were subjected to a square root transformation to approximate normality. A sequential Bonferroni test was applied to determine significance of the resulting probability values. All significant differences marked in the figures pass the sequential Bonferroni test, except for one instance described hereinafter in FIG. 1, in which significance was shown using Fisher's Exact Test. All figures shown in this manuscript present the means +SEM of the untransformed datasets.

RESULTS

Figure 2:
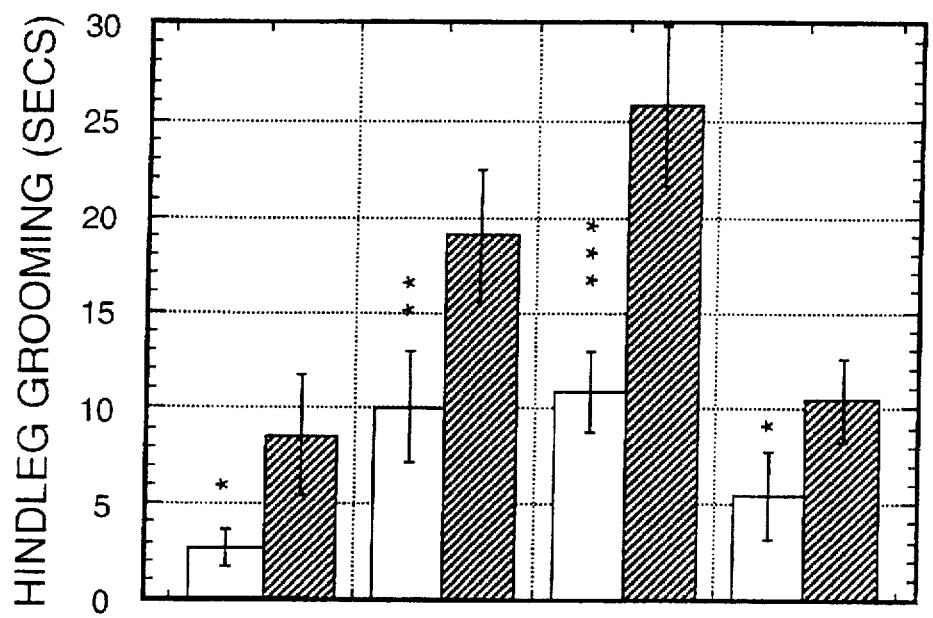
FIG. 2 is a graph depicting decapitated Drosophila hindleg grooming in response to hydrazaline and amines.

To determine the effects of exogenous biogenic amines, amines were added to the cut nerve cord of decapitated flies. As illustrated in FIGS. 1 and 2, locomotion and hindleg grooming were assayed in flies for 2 min intervals following application of a buffer or 10 mM amines, either alone (open bars), or in conjunction with 1 mM hydrazaline (grey bars), an inhibitor of vertebrate monoamine oxidase. In FIGS. 1 and 2 the following is applicable: BUFFER: buffer control; DA: dopamine; OCT: octopamine; 5HT: serotonin. Data show the means +SEM from n=30 observations for each condition, except for n=90 for those exposed to buffer or buffer plus hydrazaline. Significance levels for differences as a function of hydrazaline are indicated by vertical asterisks, using square root transformed datasets for calculations. *: $P<0.05$; : $P<0.005$; *: $P<0.0005$. Significance of the stimulation of locomotion by hydrazaline compared to buffer alone was determined using by comparing the fractions of flies locomoting >1 mm: 9 of 29 flies locomote after hydrazaline exposure, versus none of 90 exposed to buffer alone ($P<0.0001$, Fisher's Exact Test).

Locomotion, shown in FIG. 1, and hindleg grooming, illustrated in FIG. 2, are both stimulated significantly by the amines dopamine and octopamine, with octopamine showing a particularly strong stimulation of locomotion. Each of the locomotor responses is significant to $P<0.007$ when comparing amine vs. buffer. As can clearly be seen from the graphs of FIGS. 1 and 2, when only a buffer was added, no locomotion was observed in the 90 decapitated flies examined. Although locomotion was significantly stimulated ($P=.0.007$) using serotonin, the stimulation of hindleg grooming was not significant ($P=0.16$). Stimulation of hindleg grooming by octopamine and dopamine are both significant to $P<0.001$.

The major degradative route for dopamine and other biogenic amines in vertebrates is via monoamine oxidase (MAC) enzymes. Only extremely low levels of MAO have been detected in Drosophila, and MAO activity is not detectable in many other insects. The 1 mM hydrazaline was added to the buffer, or amines, to see whether this treatment would potentate the responses. Hydrazaline, in combination with the buffer, increased the hyperactive state and scissoring only at higher doses. Addition of hydrazaline with either buffer or amines leads to increases in both locomotion and hindleg grooming, with significant increases indicated by asterisks. Hydrazaline stimulates hindleg grooming when added either alone or in conjunction with each of the amines, and significantly stimulates locomotion when added in conjunction with either dopamine or serotonin.

Hydrazaline apparently produces the increased activity by increasing levels of endogenous amines as well as by increasing the effective dose of exogenously applied amine. Consistent with this mode of hydrazaline action, 10 mM hydrazaline was injected into 3rd instar larvae results resulting in lethality with dark pigmentation. Treatment of the decapitated flies with >5 mM hydrazaline leads to increased locomotion alternating with periods of hyperactivity (data not shown).

Figure 3:
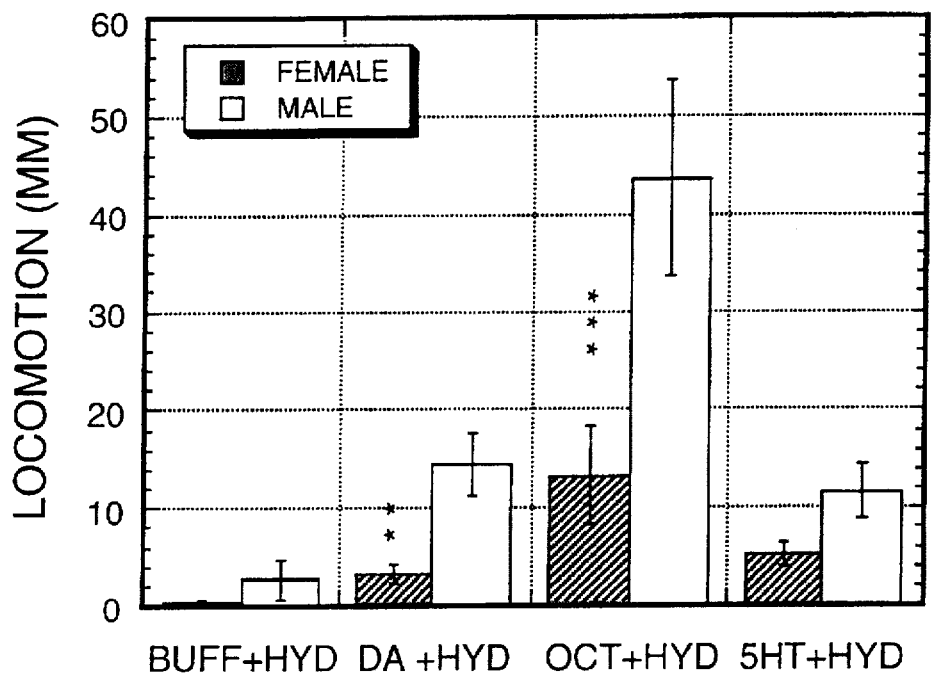
FIG. 3 is a graphic representation of the responses to the hydrazaline combinations of FIG. 1 broken down by sex.
Figure 4:
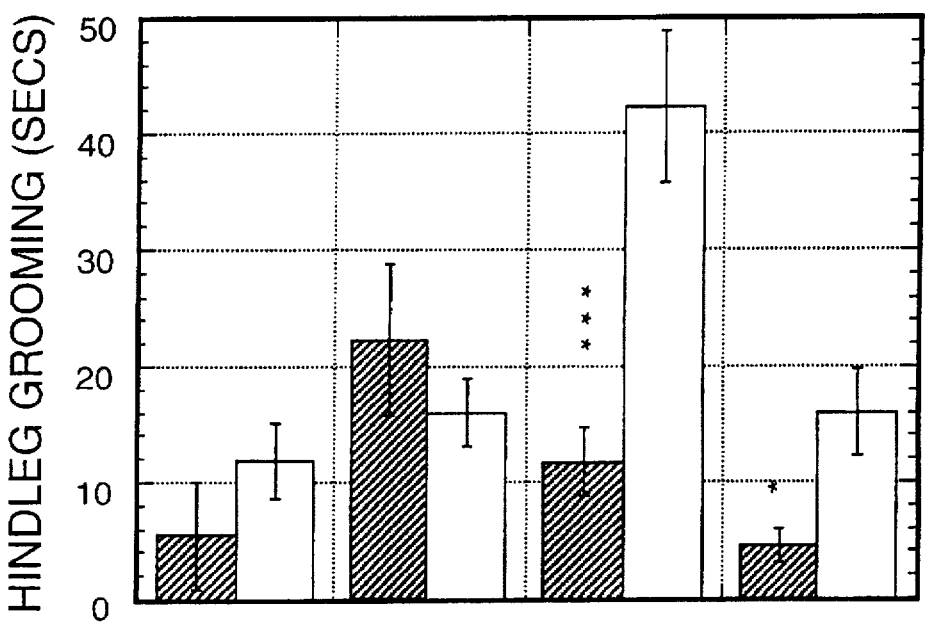
FIG. 4 is a graph representing the responses to the hydrazaline combinations of FIG. 2 broken down by sex.

Many of the effects of hydrazaline on locomotion and hindleg grooming show sexual dimorphisms, as shown in FIGS. 3 and 4, with significant differences marked by vertical asterisks. For all of the significant differences, males show increased activity relative to females. The most striking dimorphisms in both locomotion and grooming are induced by octopamine in the presence of hydrazaline, which stimulates these behaviors 3–4 fold as strongly in males vs. females. No significant sexual dimorphisms are observed when amines are added without hydrazaline.

Data were gathered and analyzed as per FIGS. 1 and 2, except that effects are plotted separately for each sex. Data are from n=15 flies for each condition, except for n=45 for each sex exposed to buffer. Significant differences indicated by asterisks as per FIGS. 1 and 2.

Examination was made to determine whether agents active on vertebrate amine receptors would be active in this system. A number of serotonin receptor agonists and antagonists showed only minor effects (data not shown), but drugs affecting vertebrate dopamine receptors show striking effects. As show in the graph of FIG. 5, a D1-like against, SKF 82958, leads to a ~5 fold stimulation of hindleg grooming as compared to the buffer ($P<0.001$). The application of SKF 82958, however, resulted in no stimulation of locomotion. Another D1-like agonist, SKF 81297, shows identical responses (data not shown) in both increased hindleg grooming and no additional locomotion.

A D1-like antagonist, SCH 23390, produced a striking phenotype of akinesia associated with a 10–15 hz tremor, with a total loss of responsiveness to mechanical stimulation. The SCH 23390 treated flies often fall on their sides with distally extended wings and outstretched legs, a phenotype resembling heavy $CO_2$ sedation. An identical phenotype was also seen with the D1-like antagonist SKF 85366.

Figure 5:
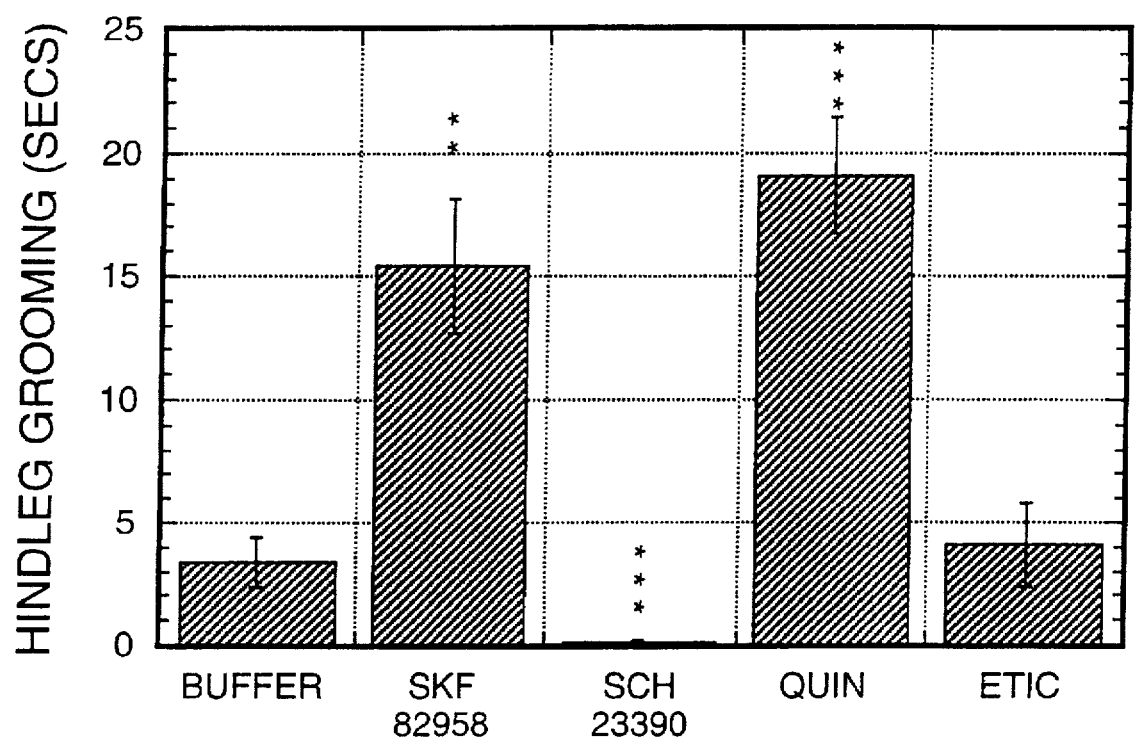
FIG. 5 is a graph illustrating drosophila hindleg grooming in response to D1 and D2 antagonists and agonists; and, FIG. 6 is a graph showing drosophila locomotion, by sex, in response to D2-like agonist quinpirole.
Figure 6:
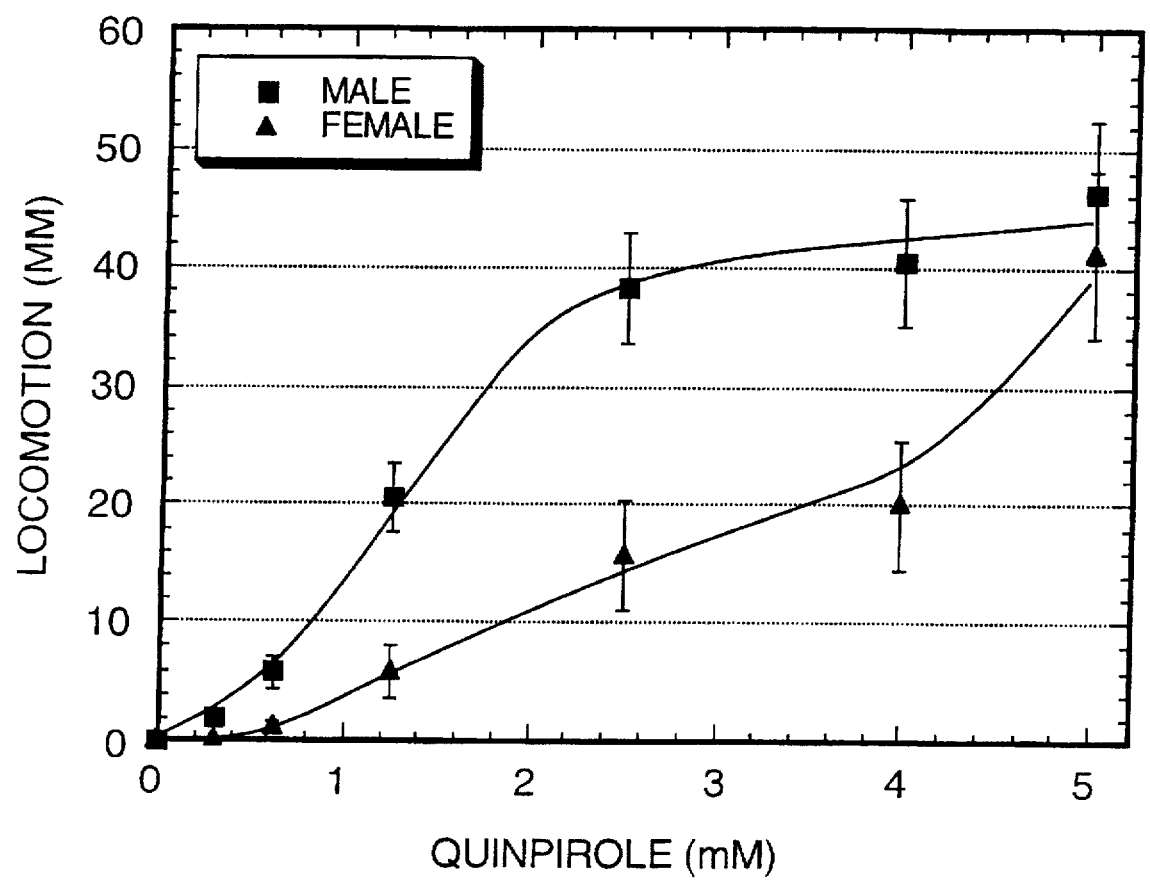

A D2-like agonist, quinpirole, illustrated in FIG. 5, shows strong effects on both hindleg grooming and locomotion. At 5 mM quinpirole, levels of hindleg grooming are stimulated ~6 fold as compared to application of the buffer. As can be seen in FIG. 6, locomotion is stimulated strongly by quinpirole. The quinpirole treated flies also show significant periods of hyperactive behaviors, similar to the hyperactivity induced by dopamine. When exposed to 5 mM quinpirole males were hyperactive for 15+10 secs, whereas females showed no hyperactivity. At higher quinpirole concentrations, hyperactivity is seen in both sexes (data not shown).

A D2-like antagonist, eticlopride, shown in FIG. 5, shows no significant effects on hindleg grooming when added at 5 mM, but rather leads to a loss of responsiveness. When eticlopride treated flies were overturned, none of 20 flies were able to right themselves, and lacked any of the vigorous righting behaviors that are observed in decapitated, untreated flies. When flies were exposed to 10 mM eticlopride, 18 of 35 flies showed an extreme phenotype in which they fell on their sides or upside down with legs withdrawn and almost motionless, and totally unresponsive to mechanical provocation. There is no visible tremor as seen with D1-like antagonists. Similar results were observed with the D2-like antagonist raclopride.

In FIG. 5, flies were exposed to: Buffer: NaPi, pH 6.0; 5 mM SK 82958, a D1-like dopamine receptor agonist; 2 mM SCH 23390, a D1-like dopamine recaptor antagonist; 5 mM quinpirole, a D2-like dopamine receptor agonist; 5 mM eticlopride, a D2-like dopamine receptor antagonist. n=28 to 32 for each drug. Quinpirole, SCK 82958, and SCH 23390 each have highly significant effects on hindleg grooming. The low level of hindleg grooming remaining after SCH 23390 treatment resulted from one fly that groomed for 2 secs immediately after application of the drug. There is no significant sex specificity for any of the effects shown.

The similarity in the responses to dopamine and octopamine to quinpirole lead to examination of the sex specificity of the quinpirole response. FIG. 6 shows the locomotor response to quinpirole as a function of quinpirole concentration. Maximal levels of locomotion of ~45 millimeters/2 min are attained in both sexes at 5 mM quinpirole. N=13 to 15 for each datapoint.

At higher quinpirole concentrations hyperactive behaviors predominate and limit overall locomotion. At low quinpirole concentrations males are selectively stimulated by quinpirole, with the concentration of quinpirole leading to half-maximal activity differing by 3–4 fold in males vs. females. This is most simply consistent with a sex specific increase in receptor affinity in males vs. females, although more complicated explanations, such as expression of different receptor types in males vs. females, cannot be discerned until the relevant receptors are identified. Modulation of seven transmembrane-helix receptor sensitivity by phosphorylation is a hallmark of this family of receptors, and this modulation can change affinities for agonists. Changes in amine receptor sensitivity or in types of receptors have not been previously linked to sexual dimorphisms.

These results indicate that differences in amine receptor sensitivity or in types of receptors expressed will be associated with sexually dimorphic behaviors in Drosophila. There is one instance in which such behaviors have been linked to biogenic amines in Drosophila. The mutant inactive (iav) affects activity levels, experience dependent conditioned male courtship behaviors, and also octopamine levels, which are 15% of wildtype. The locomotor inactivity in this mutant is consistent with the strong locomotor stimulation by octopamine in the decapitated flies. In apparent contrast with these results is a recent report generating octopamine deficient flies via mutation of tyramine B-hydroxylase, which shows only an egg retention defect. However, the mild phenotypes could be associated with the increased tyramine levels found in these flies, which may be capable of supplanting some but not all the roles of octopamine.

Additional tests were also conducted, as set forth above, using DOPA, norepinephrine and tyramine in this assay (data not shown). DOPA and norepinephrine showed no significant effects. Tyramine, the metabolic precursor to octopamine, generates behaviors similar to, but much milder than, the behaviors generated by octopamine, potentially explained by in vivo metabolism to octopamine. Only slight effects on grooming by the forelegs were observed (data not shown), and grooming by the middle legs was rarely observed and was not quantitated.

Each of the amines produced additional response differences that distinguish the neurological reaction to the different amines. Octopamine leads to rapid wing scissoring in ~50% of the flies, a behavior that is not observed with either serotonin or dopamine. Additionally, dopamine treated animals show significant amounts of hyperactive behavior, spending 11 5 seconds in a hyperactive state, with 5 of 29 flies showing hyperactivity. This behavior was not observed with either serotonin or octopamine in observations of 28 or 43 flies, respectively. From these results, it is evident that the amines dopamine, octopamine, and serotonin are leading to separate distinguishable responses in the decapitated flies.

As disclosed herein, decapitated flies are an active preparation for the study of neurally acting drugs. It is further shown that the biogenic amines dopamine, serotonin, and octopamine can stimulate grooming, locomotion, and hyperactive behaviors in similar but distinct manners. Actions of the amines, and particularly dopamine, can be mimicked by drugs that stimulate vertebrate dopamine receptors, and antagonists lead to akinesic states. Additionally, several striking sexual dimorphisms are shown in the activities of the amines and quinpirole, with greater activity in males than in females.

The foregoing indicates that none of the heretofore identified amine receptors in Drosophila is involved in the nerve cord responses assayed in the decapitated preparations. In prior art studies two D1 like dopamine receptors, and one octopamine/tyramine receptor have been identified in Drosophila, as well as a number of serotonin receptors. D2-like dopamine receptors have not been isolated from Drosophila, but if highly divergent in sequence from vertebrate receptors, may have eluded detection. Both of the known D1-like dopamine receptors are localized primarily, if not exclusively to the brain, thus excluding them from consideration in the disclosed invention. The locust homolog of the Drosophila tyramine/octopamine receptor is expressed widely in the CNS, including in the nerve cord. However, the Drosophila tyramine/octopamine receptor responds more strongly tyramine than octopamine for adenylyl cyclase inhibitory responses, and equally to both compounds when cytosolic $Ca^{++}$ release is assayed. These result are not consistent with the weak effects of tyramine relative to octopamine in the decapitated flies.

The foregoing indicate that vertebrate D1-like and D2-like dopamine receptor agonists stimulate distinct behaviors that are most simply compatible with these agents interacting with distinct receptor. The vertebrate D1-like agonists SKF 82958 and SKF 81297 selectively stimulate hindleg grooming, whereas the D2-like agonist quinpirole stimulates both hindleg grooming and locomotion. Similarly, D1-like and D2-like antagonists lead to distinguishable akinesic and unresponsive states. Decapitated flies treated with D1-like antagonists show an akinesic state with an associated tremor and extended posture, whereas D2-like antagonists cause an akinesic state without tremor and with contracted legs.

The fullest behavioral responses to dopamine agonists are seen with the D2-like agonist quinpirole. Quinpirole responses bear overlapping resemblances to the responses to dopamine, serotonin and octopamine, but with the best qualitative resemblance to the dopamine stimulated behaviors. Quinpirole leads to high levels of locomotor activity and hindleg grooming, with periods of hyperactivity. Similar behaviors are induced by dopamine, although the magnitude of responses is smaller. The response to octopamine is similar in that locomotion and grooming are strongly stimulated, but differ from quinpirole responses in that hyperactive behaviors are not observed, and many flies show rapid wing scissoring. Serotonin generates rather weak locomotor and grooming responses, and also does not lead to hyperactivity.

Given the above arguments, until the receptor(s) mediating these responses are identified, the possibility that multiple amines could be interacting with a single novel receptor subtype and activating it in different manners cannot be eliminated. Evidence for such a novel receptor has been generated from binding studies using honeybee brain extracts. These workers identified a D2-like antagonist binding activity that could be competed more strongly by octopamine and tyramine than by dopamine.

The responses of decapitated Drosophila show many resemblances to the effects of vertebrate dopamine receptor agonists and antagonists after injection into rodents. Both D1-like and D2-like receptor agonists stimulate locomotion and stereotyped behaviors, with differences in the types of stereotypes induced, and both D1-like and D2-like antagonists lead to an akinesic state. Stereotyped behaviors include behaviors such as grooming, sniffing, chewing and posturing, behaviors that are controlled by spinal cord neural oscillators. In decapitated Drosophila, stimulation of both hindleg grooming and locomotion with the D2-like agonist quinpirole is seen, whereas D1-like agonists selectively stimulate hindleg grooming without stimulating locomotion. D1-like antagonists lead to a totally akinesic state accompanied by tremor, and D2-like antagonists show a similar but distinguishable phenotype of loss of motility and responsiveness, but with no detectable tremor and a different body posture.

These phenotypic similarities are striking, indicating that these compounds are interacting with receptors analogous to the vertebrate dopamine receptors, and that the link to locomotor and stereotyped grooming behaviors occurred very early in evolution, before the split between Drosophila and vertebrates.

One important and obvious distinction between the results obtained in vertebrates and in the decapitated Drosophila is that the brain has been removed from these preparations. The vertebrate behavioral responses to dopamine depend on striatal dopamine receptors. It thus indicates that the insect nerve cord contains functions that have been taken over by the forebrain in higher vertebrates.

The high concentrations of drugs needed in the decapitated preparations are due to poor diffusion through the CNS. Observations show that serotonin, in and dopamine have limited capacity for diffusion in the Drosophila CNS. Ddc null gynandromorphs generated using an unstable ring-X Ddc$^+$ chromosome show that serotonin has only a very low capability for diffusion between segments in the larval nerve cord, diffusing only into the adjacent segment and across the midline. In recently generated lines containing tyrosine hydroxylase transgenes resulting in altered spatial patterns of dopamine expression, some of these lines show high levels of dopamine in some cells of the larval and adult brain lobes, but very low levels in other cells whose cell bodies are located within ™20 microns of neuronal projections containing high levels of dopamine. This observation indicates that diffusion and uptake into these neighboring cells must be very inefficient. The amines and amine receptor acting drugs are diffusing or are transported via the descending aminergic fibers that extend from the brain lobes into the nerve cord, explaining why exogenously applied amines are having such striking effects in the decapitated preparations, by reaching regions of the nerve cord that are normally supplied with amines released by the brain.

Since other modifications and changes varied to fit particular operating requirements and environments will be apparent to those skilled in the art, the invention is not considered limited to the example chosen for the purposes of disclosure, and covers all changes and modifications which do not constitute departures from the true spirit and scope of this invention.

What is claimed is:

1. A method of screening for neuroactive agents which modulate a behavior mediated by cellular receptors, comprising the steps of:

(a) decapitating an invertebrate;

(b) applying a reagent to the exposed nerve cord on the decapitated invertebrate; and (c) observing the effect of the reagent on the behavior mediated by cellular receptors, wherein modulation of said behavior indicates that said reagent is a neuroactive reagent.

2. The method of claim 1 wherein said invertebrate is a drosophila melanogaster.

3. The method of claim 1 wherein said reagent modulates behavior affected by cellular receptors for biogenic amines.

4. The method of claim 1 wherein said reagent modulates behavior affected by cellular receptors the for cholinergic system.

* * * * *